United States Patent
Sode et al.

(10) Patent No.: US 11,608,515 B2
(45) Date of Patent: Mar. 21, 2023

(54) BIOSENSING METHOD

(71) Applicant: ARKRAY, Inc., Kyoto (JP)

(72) Inventors: Koji Sode, Tokyo (JP); Inyoung Lee, Tokyo (JP); Wakako Tsugawa, Tokyo (JP)

(73) Assignee: ARKRAY, INC., Kyoto (JP)

( * ) Notice: Subject to any disclaimer, the term of this patent is extended or adjusted under 35 U.S.C. 154(b) by 16 days.

(21) Appl. No.: 16/417,944

(22) Filed: May 21, 2019

(65) Prior Publication Data

US 2019/0360018 A1 Nov. 28, 2019

(30) Foreign Application Priority Data

May 22, 2018 (JP) .............................. JP2018-097997

(51) Int. Cl.
*C12Q 1/00* (2006.01)
*G01N 27/327* (2006.01)
*C12Q 1/26* (2006.01)

(52) U.S. Cl.
CPC ............... *C12Q 1/001* (2013.01); *C12Q 1/26* (2013.01); *G01N 27/3275* (2013.01)

(58) Field of Classification Search
CPC .. G01N 27/3275; G01N 27/327; C12Q 1/001; C12Q 1/126; C12Q 1/00; C12Q 1/54
See application file for complete search history.

(56) References Cited

U.S. PATENT DOCUMENTS

| | | | |
|---|---|---|---|
| 5,413,690 A | 5/1995 | Kost et al. | |
| 6,770,190 B1 | 8/2004 | Milanovski et al. | |
| 2007/0131547 A1* | 6/2007 | Nomoto | H01M 8/16 204/403.01 |
| 2008/0116070 A1 | 5/2008 | Ishige et al. | |
| 2008/0164154 A1* | 7/2008 | Purvis | C12Q 1/004 205/777.5 |

(Continued)

FOREIGN PATENT DOCUMENTS

| | | |
|---|---|---|
| CN | 104520700 A1 | 4/2015 |
| EP | 1661516 A1 | 5/2006 |

(Continued)

OTHER PUBLICATIONS

Extended European Search Report issued in corresponding European Patent Application No. 19175802.8 dated Nov. 11, 2019.

(Continued)

*Primary Examiner* — Gurpreet Kaur

(74) *Attorney, Agent, or Firm* — Morgan, Lewis & Bockius LLP

(57) ABSTRACT

A method for quantifying a target substance, comprising: bringing a sample containing the target substance into contact with a biosensor which comprises an enzyme electrode containing an oxidoreductase and a counter electrode; measuring a change in the potential difference between the enzyme electrode and the counter electrode due to oxidation reaction of the target substance catalyzed by the oxidoreductase; and calculating the concentration of the target substance based on the change in the potential difference; wherein a potential is applied between the enzyme electrode and the counter electrode before the measurement of the change in the potential difference.

19 Claims, 11 Drawing Sheets

(56) References Cited

U.S. PATENT DOCUMENTS

| | | | |
|---|---|---|---|
| 2012/0094367 A1 | 4/2012 | Sugiyama et al. | |
| 2014/0021068 A1* | 1/2014 | Arimoto | G01N 27/3277 |
| | | | 205/783.5 |
| 2015/0129425 A1 | 5/2015 | Tsukada et al. | |
| 2016/0177365 A1* | 6/2016 | Katsuki | G01N 27/3272 |
| | | | 204/403.14 |
| 2019/0004005 A1* | 1/2019 | Oja | C12Q 1/001 |

FOREIGN PATENT DOCUMENTS

| | | |
|---|---|---|
| EP | 3032250 A1 | 6/2016 |
| EP | 3037812 A1 | 6/2016 |
| EP | 3078965 A1 | 10/2016 |
| EP | 3220138 A1 | 9/2017 |
| EP | 3249050 A1 | 11/2017 |
| EP | 3415634 A1 | 12/2018 |
| GB | 2421951 A | 7/2006 |
| JP | 2008-519973 A | 6/2008 |
| WO | 01/21827 A1 | 3/2001 |
| WO | 2008/035748 A1 | 3/2008 |
| WO | 2014/002999 A1 | 1/2014 |

OTHER PUBLICATIONS

Kakehi et al., "A novel wireless glucose sensor employing direct electron transfer principle based enzyme fuel cell," Biosensors and Bioelectronics, 22:2250-2255 (2007).

Lakard et al., "Urea potentiometric enzymatic biosensor based on charged biopolymers and electrodeposited polyaniline," Biosensors and Bioelectronics, 26:4139-4145 (2011).

Song et al., "Design and preparation of open circuit potential biosensor for in vitro and in vivo glucose monitoring," Analytical and Bioanalytical Chemistry, 409: 161-168 (2017).

Office Action issued in corresponding Chinese Patent Application No. 201910423091.2 dated Aug. 9, 2022.

Office Action dated Nov. 8, 2022, issued in corresponding Japanese Patent Application No. 2019-094945.

* cited by examiner

BIOSENSING METHOD

BACKGROUND OF THE INVENTION

Field of the Invention

The present invention relates to a novel biosensing method utilizing an electrochemical enzyme electrode.

Description of the Related Art

Non-patent Document 1 discloses a biofuel cell using glucose dehydrogenase (GDH) for an anode, wherein the enzyme chemically cross-linked to the electrode reacts with a substrate in an electrolyte solution to increase the potential between the anode and the cathode in proportion to the concentration of glucose as the substrate, which enables measurement of the glucose concentration by monitoring of the potential between the two electrodes.

Non-patent Document 2 discloses an enzyme electrode having a combination of an enzyme and a conductive polymer, wherein the enzyme reacts with urea as a substrate to cause a change in the electronic state of the conductive polymer, which can be detected as an interelectrode potential, enabling measurement of the substrate concentration.

Non-patent Document 3 discloses an implantable sensor using an electrode containing glucose oxidase and porous carbon, which sensor measures changes in the open circuit potential (OCP) between electrodes due to generation of hydrogen peroxide.

PRIOR ART DOCUMENTS

Non-Patent Documents

[Non-patent Document 1] Kakehi et al. Biosensors and Bioelectronics 22 (2007) 2250-55
[Non-patent Document 2] B. Lakard et al. Biosensors and Bioelectronics 26 (2011) 4139-4145
[Non-patent Document 3] Y. Song et al. Anal Bioanal Chem. 2017 409 (1) 161-168

SUMMARY OF THE INVENTION

In Non-patent Document 1, a change in the open circuit potential (OCP) for the glucose concentration in the anode is observed as an increased potential. However, since the increase depends on the consequent potential conditions, the responding time of the sensor signal varies, and loss of resolution occurs due to saturation at a high concentration close to the capacity limit of the electrode.

In Non-patent Document 2, since transfer of electrons generated by the enzymatic reaction to the conductive polymer is regarded as a signal change, noise may be produced, in principle, by changes in conditions of the conductive polymer due to factors other than the enzymatic reaction (including physical changes such as swelling). Moreover, the degree of uniformity of the coating of the conductive polymer may influence the sensor performance. Moreover, continuous use as a sensor may lead to a problem in stability of the enzyme-immobilized film.

Non-patent Document 3 discloses the principle of the so-called first generation glucose sensor, wherein oxygen is used as an electron acceptor of an enzyme. Hydrogen peroxide generated by enzymatic reaction functions as a molecule that causes the potential change. However, there is a concern that hydrogen peroxide may have an irreversible effect on the sensor surface material because of its instability and oxidation capacity.

Accordingly, an object of the present invention is to provide a method that enables accurate, stable, and long-term quantitative measurement of a substance.

In order to solve the above problems, the present inventors intensively studied and found that highly reproducible, stable measurement of the concentration of a substrate can be achieved by allowing a sample containing the substrate (measurement target substance) to react with a sensor containing an enzyme electrode having an oxidoreductase immobilized thereon and a counter electrode, applying a certain potential between the enzyme electrode and the counter electrode for a certain period of time, and then measuring the potential difference (OCP) between the enzyme electrode and the counter electrode.

The present invention can be summarized as follows.

[1] A method for quantifying a target substance comprising:
 bringing a sample containing the target substance into contact with a biosensor which comprises an enzyme electrode containing an oxidoreductase and a counter electrode;
 measuring a change in the potential difference between the enzyme electrode and the counter electrode due to an oxidation reaction of the target substance catalyzed by the oxidoreductase; and
 calculating the concentration of the target substance based on the change in the potential difference;
 wherein a potential (voltage) is applied between the enzyme electrode and the counter electrode before the measurement of the change in the potential difference.
[2] The method according to [1], wherein the change in the potential difference between the enzyme electrode and the counter electrode is a change from a value of the potential applied between the enzyme electrode and the counter electrode.
[3] The method according to [1] or [2], wherein the potential applied between the enzyme electrode and the counter electrode is not less than −100 mV as evaluated using a silver/silver chloride electrode as a reference.
[4] The method according to any one of [1] to [3], wherein the potential between the enzyme electrode and the counter electrode is applied for not less than 0.1 seconds.
[5] The method according to any one of [1] to [4], wherein the oxidoreductase is an oxidoreductase capable of direct transfer of electrons with the enzyme electrode.
[6] The method according to [5], wherein the oxidoreductase is an oxidoreductase containing an electron transfer subunit or an electron transfer domain.
[7] The method according to [6], wherein the electron transfer subunit or the electron transfer domain contains heme.
[8] The method according to any one of [1] to [7], wherein the substance is glucose, and the oxidoreductase is glucose dehydrogenase.
[9] An apparatus for measuring a substance comprising:
 a biosensor comprising an enzyme electrode containing an oxidoreductase and a counter electrode;
 a control section configured to control the application of a potential (voltage) to the enzyme electrode of the biosensor;
 a measurement section configured to measure a change in the potential difference between the enzyme electrode and the counter electrode of the biosensor;
 an arithmetic section configured to calculate the concentration of the target substance from the change in the potential difference; and an output section configured to output the calculated concentration of the target substance.

According to the present invention, by using an electrode containing an oxidoreductase, and measuring the potential difference (OCP) between this electrode and a counter electrode, a change in the electron state of the enzyme, which reflects the substrate concentration in the system, can be determined.

In the method of the present invention, the electron state of the enzyme is directly monitored based on the potential difference rather than indirectly monitoring the current value using a conductive polymer or an electron acceptor. The method is therefore less susceptible to noise caused by external factors. Moreover, unlike methods in which the natural potential between two electrodes is simply continuously monitored as disclosed in the prior art documents, an operation of potential application is carried out for a certain period of time immediately before the measurement of the glucose concentration in order to recover the enzyme from the reduced state to the oxidized state. Therefore, the measurement can be started from a constant starting OCP, and a decrease in the resolution can be prevented, so that more accurate measurement is possible.

Unlike conventional methods requiring measurement under application of a constant voltage, the method of the present invention does not require continuous application of a constant voltage even for continuous measurement or repeated measurement. Therefore, turnover of the enzyme can be suppressed, and monitoring can be carried out while allowing the enzyme on the electrode to act in a very mild environment, so that highly stable measurement is possible.

DETAILED DESCRIPTION OF THE INVENTION

Figure 1:
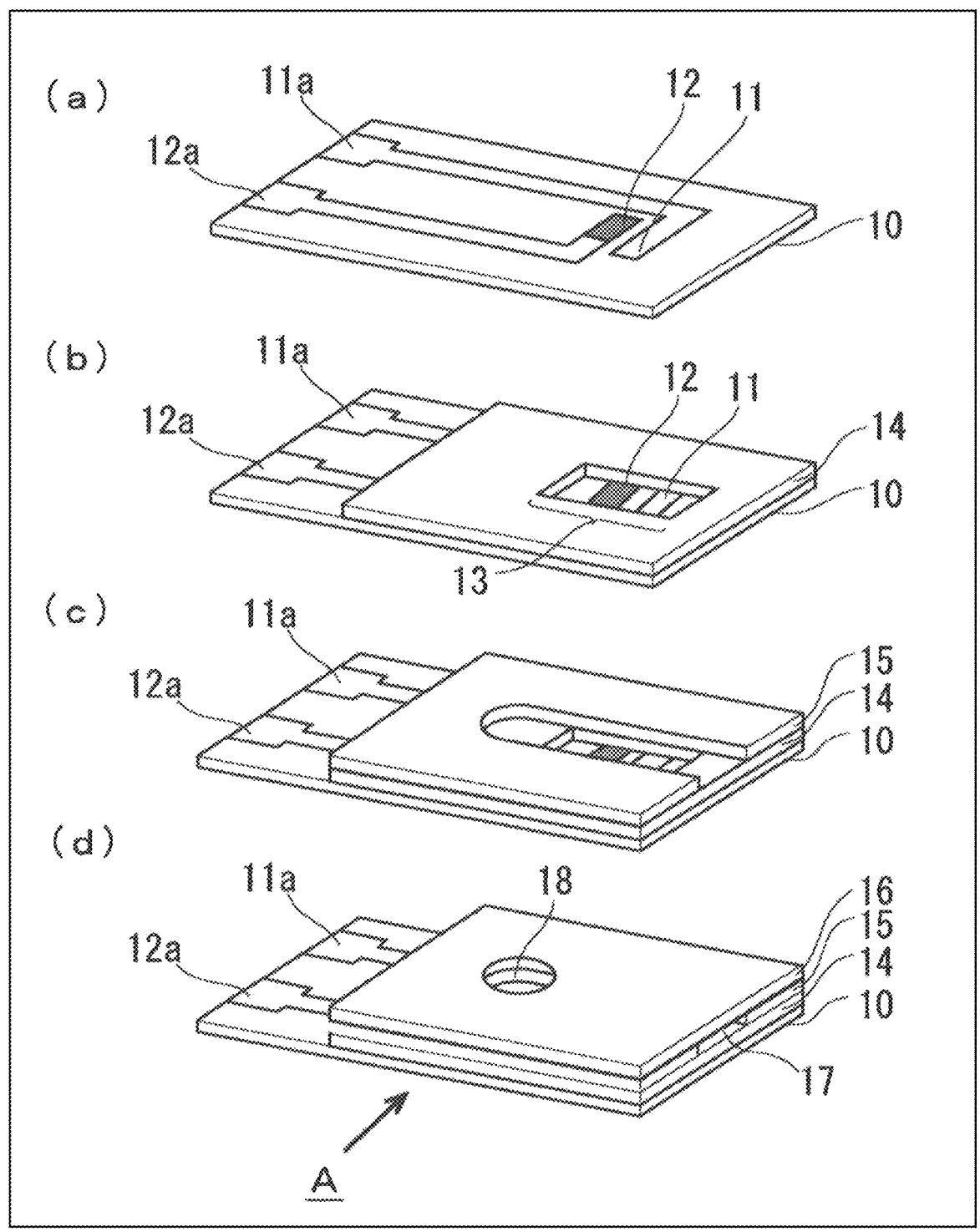
FIG. 1 shows a process chart illustrating an embodiment of a method for fabricating a biosensor. Panels (a) to (d) show schematic diagrams showing the biosensor in each step.

The method for quantifying a substance and the apparatus for measuring a substance as embodiments of the present invention are described below with reference to drawings and the like. Each embodiment described below is merely an example, and the present invention is not limited to the constitutions of the following embodiments.

The method for quantifying a target substance of the present invention is characterized in that it comprises:

bringing a sample containing the target substance into contact with a biosensor which comprises an enzyme electrode containing an oxidoreductase and a counter electrode;

measuring a change in the potential difference between the enzyme electrode and the counter electrode due to an oxidation reaction of the target substance catalyzed by the oxidoreductase; and calculating the concentration of the target substance based on the change in the potential difference;

wherein a potential is applied between the enzyme electrode and the counter electrode before the measurement of the change in the potential difference.

The target substance is not limited as long as it is a substance that can be a substrate of the oxidoreductase, and examples thereof include, but are not limited to, glucose, fructose, sorbitol, cholesterol, cellobiose, ethanol, lactic acid, and uric acid.

The sample is not limited as long as it contains the target substance. The sample is preferably a biological sample, and examples thereof include blood and urine.

(Biosensor)

The biosensor to be used in the method of the present invention comprises an enzyme electrode (working electrode) containing an oxidoreductase arranged on the electrode, and a counter electrode that forms a pair with the enzyme electrode. For application of a certain potential with respect to the counter electrode to the enzyme electrode, and for measurement of the potential difference change in the enzyme electrode, the biosensor preferably comprises a reference electrode as well as the enzyme electrode and the counter electrode. Alternatively, a silver/silver chloride electrode or a calomel electrode may be used as the counter electrode, which can also function as a reference electrode.

The counter electrode is not limited as long as it can be generally used as a counter electrode for a biosensor. Examples of the counter electrode include a carbon electrode prepared in the form of a film by screen printing, a metal electrode prepared in the form of a film by physical vapor deposition (PVD, for example, sputtering) or chemical vapor deposition (CVD), and a silver/silver chloride electrode prepared in the form of a film by screen printing. The reference electrode may be a silver/silver chloride electrode, calomel electrode, or the like.

(Enzyme Electrode)

The enzyme electrode contains an oxidoreductase arranged on the electrode.

The electrode is formed using a metallic material or a carbon material, wherein examples of the metallic material include gold (Au), platinum (Pt), silver (Ag), and palladium (Pd), and examples of the carbon material include carbons such as graphite, carbon nanotube, graphene, and mesoporous carbon. The electrode may be provided on an insulating substrate formed with an insulating material, wherein examples of the insulating material include resins (plastics) such as thermoplastic resins including polyetherimide (PEI), polyethylene terephthalate (PET), and polyethylene (PE), as well as polyimide resins and epoxy resins; glasses; ceramics; and papers.

(Oxidoreductase)

The oxidoreductase may be selected depending on the type of the target substance. Examples of oxidoreductases include glucose oxidase (GOD), galactose oxidase, bilirubin oxidase, pyruvate oxidase, D- or L-amino acid oxidase, amine oxidase, cholesterol oxidase, choline oxidase, xanthine oxidase, sarcosine oxidase, L-lactate oxidase, ascorbate oxidase, alcohol dehydrogenase, glutamate dehydrogenase, cholesterol dehydrogenase, aldehyde dehydrogenase, glucose dehydrogenase (GDH), fructose dehydrogenase, sorbitol dehydrogenase, lactate dehydrogenase, malate dehydrogenase, glycerol dehydrogenase, 17B hydroxysteroid dehydrogenase, estradiol 17B dehydrogenase, amino acid dehydrogenase, glyceraldehyde 3-phosphate dehydrogenase, 3-hydroxysteroid dehydrogenase, diaphorase, cytochrome oxidoreductase, catalase, peroxidase, and glutathione reductase. The oxidoreductase is preferably an oxidoreductase of a sugar, and examples of the oxidoreductase of a sugar include glucose oxidase (GOD), galactose oxidase, glucose dehydrogenase (GDH), fructose dehydrogenase, and sorbitol dehydrogenase. Thus, depending on the type of the enzyme, the biosensor of the present invention can be used as a glucose sensor, cholesterol sensor, ethanol sensor, sorbitol sensor, fructose sensor, cellobiose sensor, lactate sensor, uric acid sensor, or the like.

Among these, an oxidoreductase capable of direct electron transfer with the electrode, that is, an oxidoreductase capable of direct transfer of electrons generated by the enzymatic reaction to the electrode without requiring an oxidation-reduction substance such as an electron acceptor (which oxidoreductase is also referred to as direct electron transfer-type oxidoreductase) is preferably used. Examples of the oxidoreductase capable of direct electron transfer with the electrode include oxidoreductases physiologically including an oxidation-reduction molecule involved in electron transfer with the electrode. For example, an oxidoreductase containing an electron transfer subunit or an electron transfer domain as the oxidation-reduction molecule may be used. Examples of the electron transfer subunit include heme-containing subunits, and examples of the electron transfer domain include heme-containing domains. Examples of the heme-containing subunits and domains include subunits and domains containing heme C or heme b, more specifically, subunits and domains containing a cytochrome such as cytochrome C or cytochrome b.

Examples of the enzyme containing a cytochrome-containing subunit as an electron transfer subunit include glucose dehydrogenase (GDH), sorbitol dehydrogenase (sorbitol DH), D-fructose dehydrogenase (fructose DH), D-glucoside-3-dehydrogenase, cellobiose dehydrogenase, lactate dehydrogenase, and urate oxidase.

Specific examples of the glucose dehydrogenase containing a cytochrome include cytochrome glucose dehydrogenase having an FAD-containing catalytic subunit ($\alpha$-subunit) and a cytochrome subunit ($\beta$-subunit) (FADGDH), wherein the FADGDH preferably further has a regulatory subunit ($\gamma$-subunit) (FADGDH $\gamma\alpha\beta$).

Examples of the FADGDH include FAD-dependent glucose dehydrogenase derived from *Burkholderia cepacia*, and mutants thereof. Examples of the mutants of FADGDH derived from *Burkholderia cepacia* include FADGDH mutants such as an $\alpha$-subunit mutant in which the amino acid residues at positions 472 and 475 are substituted (WO 2005/103248), an $\alpha$-subunit mutant in which the amino acid residues at positions 326, 365, and 472 are substituted (QYY: JP 2012-090563 A), and an $\alpha$-subunit mutant in which the amino acid residues at positions 365, 326, 472, 475, 529, and the like are substituted (WO 2006/137283).

Examples of the enzyme containing an electron transfer domain include enzymes containing a heme domain or a cytochrome domain. Specific examples of such an enzyme include quinoheme ethanol dehydrogenase (QHEDH, PQQ Ethanol dh). Examples of the enzyme containing a cytochrome-containing domain as an electron transfer domain include "QHGDH" (fusion enzyme; GDH with heme domain of QHGDH) and cellobiose dehydrogenase. The fusion protein of PQQ glucose dehydrogenase (PQQGDH) and cytochrome disclosed in WO 2005/030807 may also be used.

Instead of using the direct electron transfer-type oxidoreductase, an oxidoreductase may be arranged on the electrode in a state where direct electron transfer with the electrode is possible, using a conductive polymer, redox polymer, or the like. For this, it is important to arrange the oxidoreductase in the vicinity of the electrode. Since the upper limit of the distance at which direct electron transfer occurs in a physiological reaction system is said to be 10 to 20 Å, it is important to arrange the enzyme at a distance shorter than this from the electrode so that electron transfer from the enzyme to the electrode is not prevented.

Oxidoreductases also include an oxidoreductase which becomes capable of electron transfer with the electrode when the enzyme is modified with an electron acceptor or a nanomaterial, or when an electron acceptor or a nanomaterial is used as a material of the electrode.

The electron acceptor herein may be a compound having no catalytic action which receives an electron from an oxidoreductase to undergo reduction, followed by reoxidization at the electrode. Examples of the electron acceptor include quinone compounds (for example, 1,4-naphthoquinone, VK3, 9,10-phenanthrenequinone, 1,2-naphthoquinone, p-xyloquinone, methylbenzoquinone, 2,6-dimethylbenzoquinone, sodium 1,2-naphthoquinone-4-sulfonate, 1,4-anthraquinone, tetramethylbenzoquinone, and thymoquinone), phenylenediamine compounds (for example, N,N-dimethyl-1,4-phenylenediamine and N,N,N',N'-tetramethyl-1,4-phenylenediamine), 1-methoxy-PMS (1-methoxy-5-methylphenazinium methylsulfate), PES (phenazine ethosulfate), coenzyme Q0, AZURE A chloride, phenosafranin, 6-aminoquinoxaline, and tetrathiafulvalene.

Examples of the method for the modification of the oxidoreductase with the electron acceptor include a method in which the electron acceptor is chemically bound to the enzyme. For example, the method may be a method in which a functional group such as succinimide is introduced to the electron acceptor, and the functional group is then reacted with an amino group of the enzyme to introduce the electron acceptor to the enzyme.

In cases where a nanomaterial is used, it is a conductive material that can be arranged at a distance at which direct electron transfer with the active center of the enzyme is possible. Examples of the nanomaterial include carbon nanotubes (Analytical Biochemistry, Volume 332, Issue 1, 1 Sep. 2004, Pages 75-83) and metal nanoparticles (Analytical Biochemistry Volume 331, Issue 1, 1 Aug. 2004, Pages 89-97). However, the nanomaterial is not limited thereto as long as the direct electron transfer can be observed.

Examples of the method for arranging the oxidoreductase on the electrode surface include, but are not limited to, a method in which the oxidoreductase is chemically immobilized on the electrode, a method in which the oxidoreductase is indirectly immobilized on the electrode using a conductive polymer, cross-linking agent, or the like (for example, WO 2014/002999 or JP 2016-121989 A), and a method in which the enzyme is immobilized on the electrode through a monolayer-forming molecule. Examples of the method in which the enzyme is immobilized on the electrode through a monolayer-forming molecule include a method in which the enzyme is immobilized on the electrode through a monolayer-forming molecule (SAM) disclosed in JP 2017-211383 A.

(Method for Preparing Enzyme Electrode)

The enzyme electrode is prepared, for example, as follows.

First, a metal layer which functions as an electrode is formed on one side of an insulating substrate. For example, a metal layer having a desired thickness (for example, about 30 nm) is formed by depositing a metallic material, by physical vapor deposition (PVD, for example, sputtering) or chemical vapor deposition (CVD), on one side of an insulating substrate in the form of a film having a predetermined thickness (for example, about 100 µm). Instead of the metal layer, an electrode layer made of a carbon material may be formed.

To the surface of the thus obtained electrode layer, an enzyme is bound.

For example, in cases where a monolayer-forming molecule is used, the monolayer-forming molecule is first bound onto the electrode. Thereafter, by reacting a reactive functional group of the monolayer-forming molecule with an amino group or a carboxyl group of an oxidoreductase, the oxidoreductase can be immobilized on the electrode through the monolayer-forming molecule.

In cases where the enzyme is immobilized onto the electrode using a conductive polymer or a cross-linking agent, the enzyme and the reagent such as a conductive polymer or a cross-linking reagent may be added onto the electrode to prepare an enzyme electrode.

(Method for Preparing Biosensor)

An example of a biosensor is described below based on FIG. 1.

Panels (a) to (d) in FIG. 1 show perspective views showing a series of steps for production of a biosensor. The biosensor is not limited to the following embodiment, and may be either an implantable sensor or a batch-type sensor.

As shown in Panel (d) of FIG. 1, the biosensor A is provided with an electrode system constituted by a substrate 10, a counter electrode 11 having a lead section 11a, and a working electrode 12 having a lead section 12a (Panel (a) of FIG. 1); an insulating layer 14; a spacer 15 in which an opening section is formed; and a cover 16 in which a penetrating hole 18 is formed. As shown in Panel (b) of FIG. 1, the substrate 10 is provided with a detection section 13, and, in the detection section 13, the working electrode 12 and the counter electrode 11 are arranged in parallel in the transverse direction of the substrate 10. An insulating section is present between the working electrode 12 and the counter electrode 11. As shown in Panel (b) of FIG. 1, the insulating layer 14 is layered on the substrate 10 provided with such an electrode system, except for the lead sections 11a and 12a and the detection section 13. An oxidoreductase is immobilized on the working electrode 12 of the detection section 13, where the insulating layer 14 is not layered. As shown in Panel (c) of FIG. 1, a spacer 15 in which an opening section is formed in the portion corresponding to the detection section 13 is arranged on the insulating layer 14. The cover 16, in which the penetrating hole 18 is formed in the portion partially corresponding to this opening section, is arranged on the spacer 15 (Panel (d) of FIG. 1). In this biosensor, the space of the opening section, which corresponds to the space surrounded by the working electrode, the counter electrode, the insulating layer 14, and the cover 16, functions as a sample supply section 17 for a capillary. The penetrating hole 18 functions as an air hole for suction of a sample by the capillary action.

(Method for Quantifying Substance)

The quantification method of the present invention comprises:

bringing a sample containing a target substance into contact with a biosensor;

measuring the change in the potential difference between the electrodes due to an oxidation reaction of the target substance catalyzed by the oxidoreductase; and calculating the concentration of the target substance based on the change in the potential difference.

The step of bringing a sample containing a target substance into contact with a biosensor may be either a step of adding the sample dropwise to the biosensor or a step of immersing the biosensor in the sample. In cases of an implantable sensor, the method also includes a step of implanting the sensor in the body to place the sensor in a state where the sensor is in contact with a sample such as blood.

By bringing the biosensor into contact with the sample containing the target substance, oxidation reaction of the substance by the oxidoreductase can be allowed to occur, resulting in an increase in the reduced enzyme depending on the substrate concentration. More specifically, since the enzyme is immobilized in the vicinity of the electrode, and the active center (more strictly, electron transfer unit) of the enzyme is adjacent to the electrode, its conversion from the oxidized form to the reduced form causes a change in the charge distribution in the electrode, leading to a change in the surface potential. Since the number of enzyme molecules converted to the reduced form in this process is dependent on the concentration of the target substance, the degree of change in the potential from a reference potential can be regarded as a parameter representing the concentration of the target substance.

In the present invention, a potential is applied to the enzyme electrode for a predetermined period of time before the OCP measurement.

By this, the electron state of the enzyme electrode can be reset, and the OCP value after the enzymatic reaction can be measured as a change from the state reset by the application of the potential. Therefore, a more accurate, reproducible, and stable measurement result can be obtained. In other words, the change in the potential difference to be measured can be a value of change from the potential applied (OCP-potential applied).

The potential to be applied is not limited as long as it is a potential higher than the oxidation-reduction potential of the oxidoreductase to be used as the sensor. For example, in cases of glucose dehydrogenase, the potential may be not less than −100 mV, not less than +10 mV, or not less than +100 mV as evaluated using a silver/silver chloride electrode as a reference. The upper limit is not limited, and may be, for example, +10,000 mV, +5000 mV, or +1000 mV as evaluated using a silver/silver chloride electrode as a reference.

The period of time of the application of the potential to the enzyme electrode is not limited as long as the electron state in the oxidoreductase can be reset, and may be not less than 0.01 seconds, not less than 0.1 seconds, or not less than 1 second. There is no upper limit of the application time, and the application time may be, for example, not more than 20 seconds or not more than 10 seconds.

The timing of the application of the potential is preferably immediately before the measurement of the target substance in the sample. In cases of continuous measurement, the potential can be applied before each time of measurement of the OCP, which is carried out at a plurality of points.

The timing of the OCP measurement for measurement of the substance concentration is preferably a timing when the change in the potential difference depending on the substrate concentration becomes stable to show a constant value after the application of the potential. Although the timing varies depending on the range of the substance concentration, it is preferably 10 to 20 seconds after completion of the application of the potential, or thereafter.

The method of the present invention is applicable to either a single measurement or continuous measurement.

In cases of a single measurement, for example, the sample may be brought into contact with the sensor, and then the potential may be applied, followed by measurement of the OCP change. In cases of continuous measurement, for example, the sample may be brought into contact with the sensor, and then the cycle of application of the potential and measurement of the OCP change may be repeatedly carried out at desired timing.

In the step of calculating the concentration of the target substance based on the change in the potential difference, for example, a calibration curve for the sensor may be prepared by preliminarily calculating the relationship between the value of the change in the potential difference and the substrate concentration, and then the measured value may be applied to the calibration curve to determine the substance concentration.

(Apparatus)

One embodiment of the measuring apparatus of the present invention is described below with reference to drawings. Although one embodiment of a glucose measuring apparatus is illustrated here as an example, the measuring apparatus of the present invention is not limited to the following embodiment.

Figure 2:
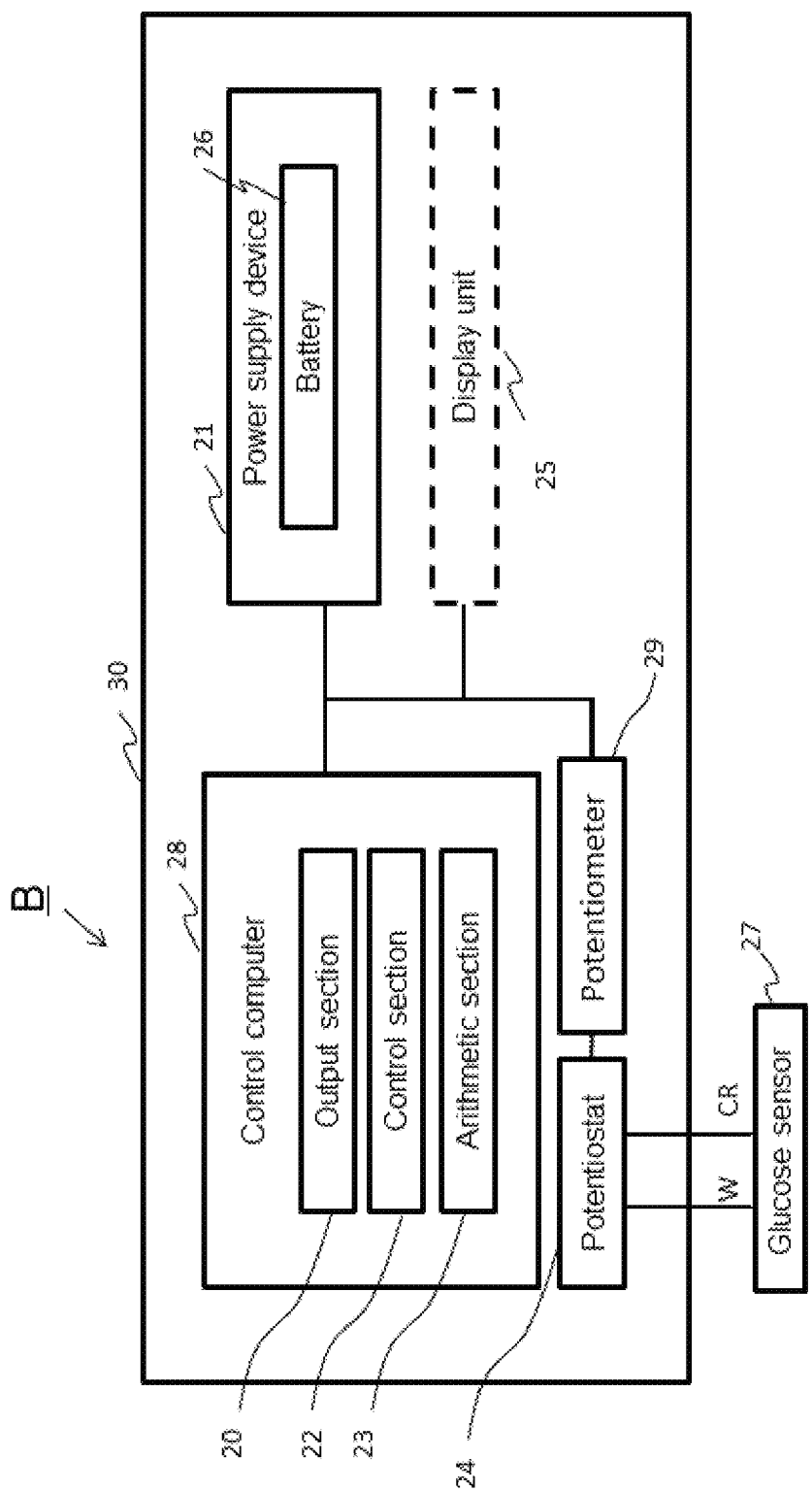
FIG. 2 shows a schematic diagram illustrating one embodiment of the measuring apparatus of the present invention.

FIG. 2 shows an example of the configuration of main electronic components included in a measuring apparatus B. A control computer 28, a potentiostat 24, a potentiometer 29, and a power supply device 21 are provided on a substrate 30 housed in a housing.

The control computer 28 includes, as hardware, a processor such as a CPU (central processing unit); a recording medium such as a memory (RAM (Random Access Memory) or ROM (Read Only Memory)); and a communication unit. When the processor loads a program stored in the recording medium (for example, the ROM) to the RAM, and executes the program, the control computer 28 functions as an apparatus provided with an output section 20, a control section 22, an arithmetic section 23, and a measurement section (the potentiostat 24 and the potentiometer 29). The control computer 28 may also include an auxiliary memory such as a semiconductor memory (EEPROM or flash memory) or a hard disk.

The control section 22 controls, for example, the timing for applying the potential and the value of the potential to be applied.

The power supply device 21 includes a battery 26, and supplies electricity to the control section computer 28 and the potentiostat 24 to allow their operation. The power supply device 21 may also be arranged outside the housing.

The potentiostat 24 is a device which keeps the potential of the working electrode constant with respect to the reference electrode. The potentiostat 24, under the control of the control section 22, applies a predetermined potential between the counter electrode and the working electrode of a glucose sensor 27 using terminals CR and W.

The potentiometer 29 measures the change in the potential difference (OCP) between the electrodes a certain length of time after the application of the potential.

The arithmetic section 23 calculates the concentration of the target substance based on the OCP measured, and stores the result. The output section 20 carries out data communication with a display section unit 25, and sends the calculated result on the concentration of the target substance provided by the arithmetic section 23 to the display section unit 25. The display section unit 25 is capable of displaying, for example, the calculated result on the glucose concentration received from the measuring apparatus B, on a display screen in a predetermined format.

Figure 3:
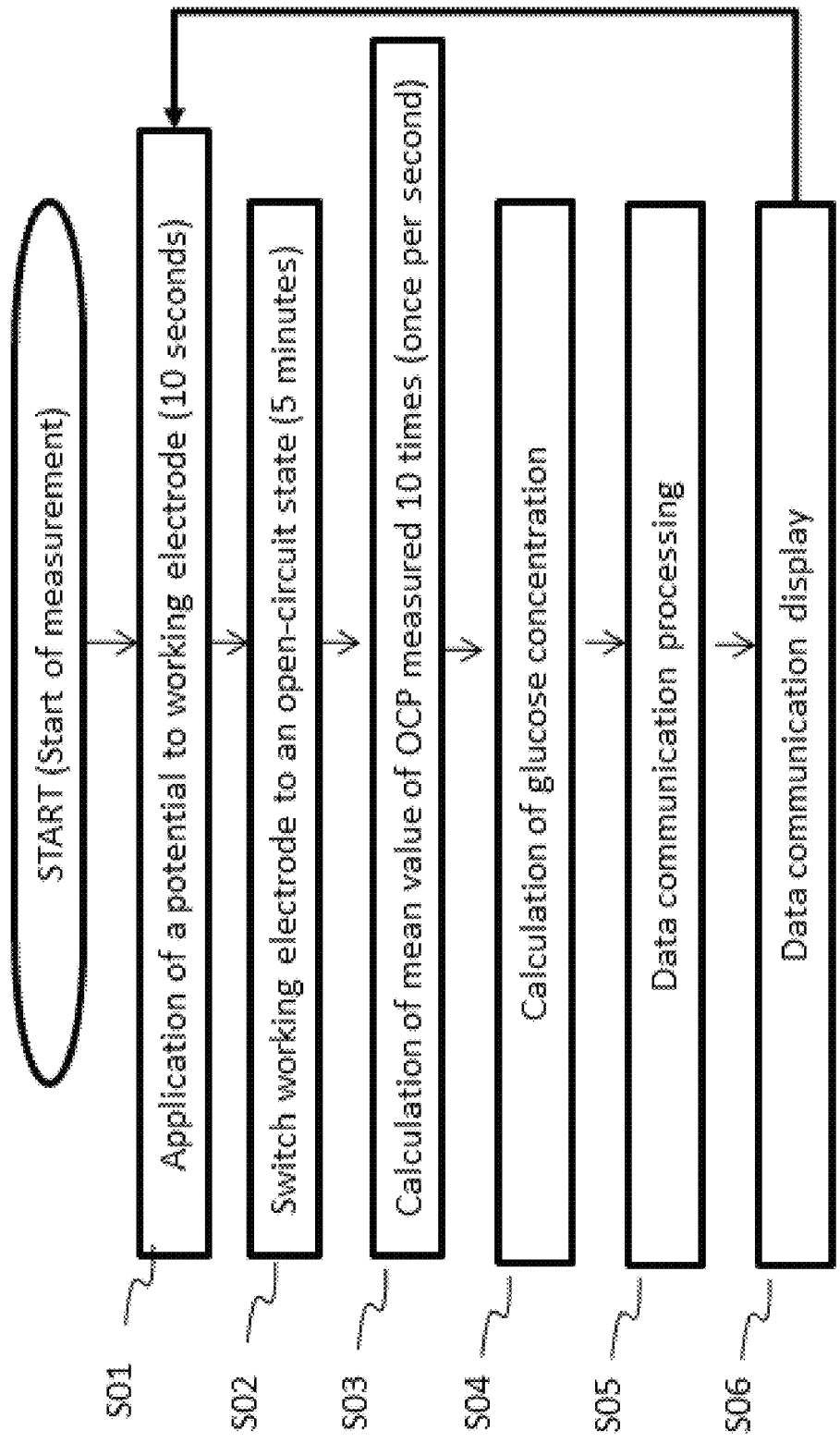
FIG. 3 shows a flow chart illustrating one embodiment of a measurement program using the measuring apparatus of the present invention.

FIG. 3 is a flow chart illustrating an example of the glucose concentration measurement process carried out by the control computer 28.

When the CPU (control section 22) of the control computer 28 receives an instruction to start the measurement of the glucose concentration, the control section 22 controls the potentiostat 24 to apply a predetermined potential to the working electrode, to start the measurement. For example, a potential of +100 mV with respect to the reference electrode is applied to the working electrode for 10 seconds (Step S01).

The control section 22 controls the potentiostat 24 to switch the working electrode to an open-circuit state, and the potentiometer 29 measures the potential difference between the working electrode 12 and the counter electrode 11 for a predetermined time (for example, 5 minutes) (Step S02). The measurement result on the potential difference is sent to the arithmetic section 23, for example, once per second.

The arithmetic section 23, for example, calculates the average of the OCP measured once per second a total of 10 times during the 10 seconds immediately before the next application of the potential (Step S03), and carries out arithmetic processing based on the value of the change in the potential difference, to calculate the glucose concentration (Step S04).

For example, the arithmetic section 23 of the control computer 28 preliminarily has calibration curve data on the value of the change in the potential difference and the glucose concentration applicable to the glucose dehydrogenase disposed on the electrode, and calculates the glucose concentration using the calculation formula or the calibration curve.

The output section 20 sends the calculated result on the glucose concentration to the display section unit 25 through a communication link provided between the output section 20 and the display section unit 25, to display the glucose concentration (Steps S05 and S06).

In cases of a plurality of times of measurement or continuous measurement, after the display of the glucose concentration, the control section 22 controls the potentiostat 24 to apply the potential to the working electrode, to start the measurement again.

EXAMPLES

The present invention is described below more concretely by way of Examples. However, the present invention is not limited to the Examples.

Example 1

Preparation of Sensor
1. Application of a mesoporous carbon dispersion (trade name, CNovel P(4)050; concentration, 1%; 10 μL) to an Au electrode (surface area, 7 mm²)
2. Application of an aqueous *Burkholderia cepacia* glucose dehydrogenase (FADGDH γαβ) (having a QYY mutation in the α-subunit) solution (0.013 mg/mL, 7 μL) and drying (for a control, application of an aqueous BSA solution (0.0128 mg/mL, 7 μL))
3. Treatment with 25% glutaraldehyde (GA) vapor for 1 hour to perform cross-linking of FADGDH γαβ to the electrode Surface Potential Measurement The enzyme electrode prepared as described above was combined with a counter electrode and a reference electrode (both of which were Ag/AgCl) to provide a biosensor, and a potential of +100 mV (vs Ag/AgCl) was applied to the enzyme electrode (3 times of 10 seconds of application), followed by immersion in a glucose solution (100 mM PPB pH 7.0, 37° C.) having a predetermined concentration (0.1, 1, 3, 5, 10, 15, or 20 mM) to cause enzymatic reaction, and measurement of the open circuit potential. This step was repeatedly carried out.

As a control, a biosensor including a BSA electrode as well as a counter electrode and a reference electrode (both of which were Ag/AgCl) was used. A potential of +100 mV was applied to the BSA electrode (1 time of 10 seconds of application), followed by immersion in a glucose solution under the same conditions to cause enzymatic reaction, and measurement of the open circuit potential. This step was repeatedly carried out.

Figure 4:
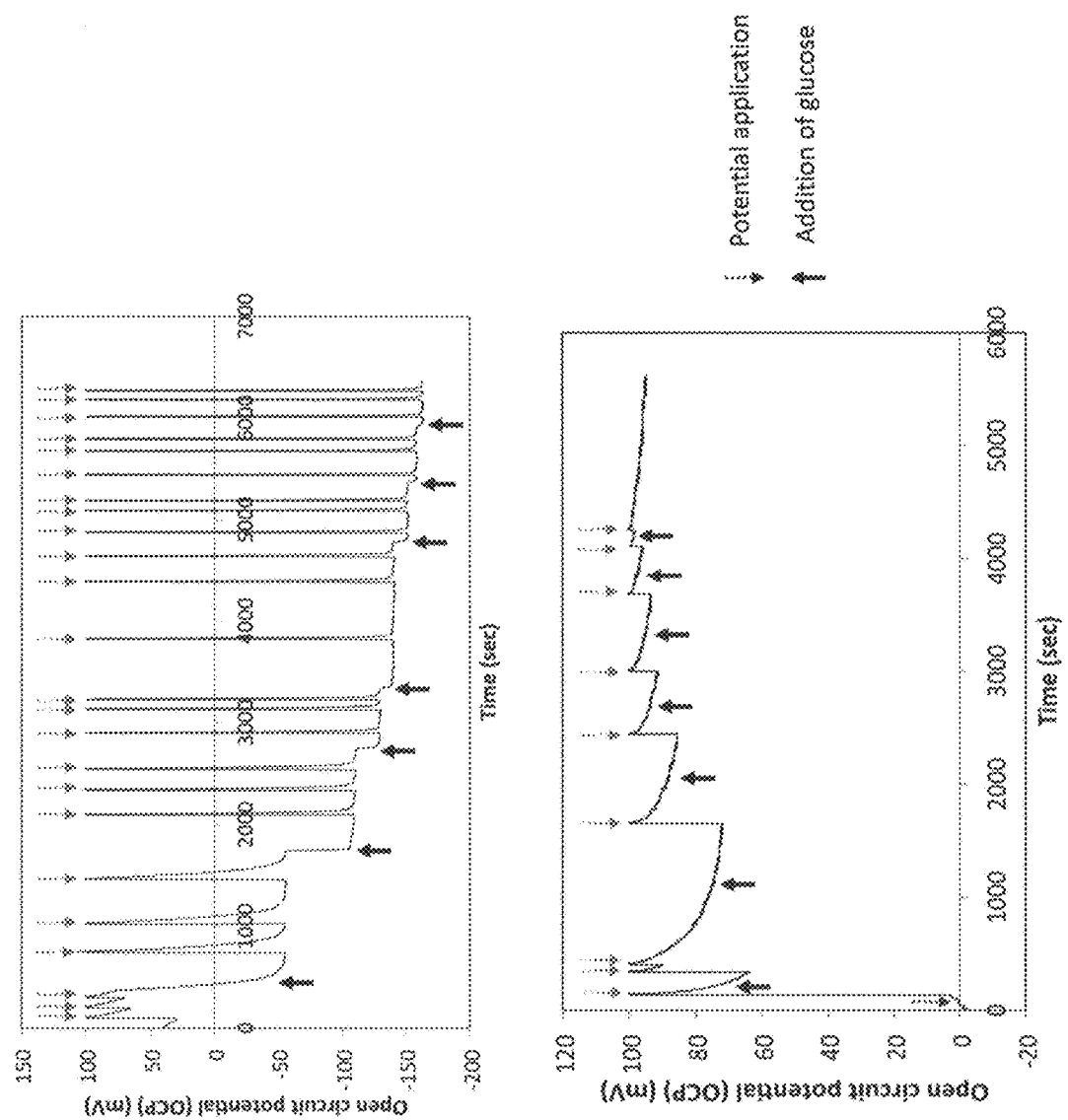
FIG. 4 shows graphs showing OCP measurement results obtained with an enzyme-immobilized electrode (upper panel) or a BSA-immobilized electrode (lower panel).

The results are shown in FIG. 4.

The non-enzyme sensor having the BSA electrode did not show a change in the OCP after the addition of the substrate (glucose). In contrast, when the external potential was applied for a short period to the enzyme sensor having the GDH electrode, the subsequent enzymatic reaction caused recovery to the potential (OCP) reflecting the glucose concentration.

Subsequently, a biosensor comprising a GDH electrode having various amounts of FADGDH γαβ immobilized thereon was used. A potential of +100 mV (vs Ag/AgCl) was applied to the GDH electrode (1 time of 10 seconds of application), and glucose was added thereto to cause enzymatic reaction, followed by measurement of the open circuit potential. This step was repeatedly carried out while changing the glucose concentration in order to investigate the relationship between the OCP and the glucose concentration.

Figure 5:
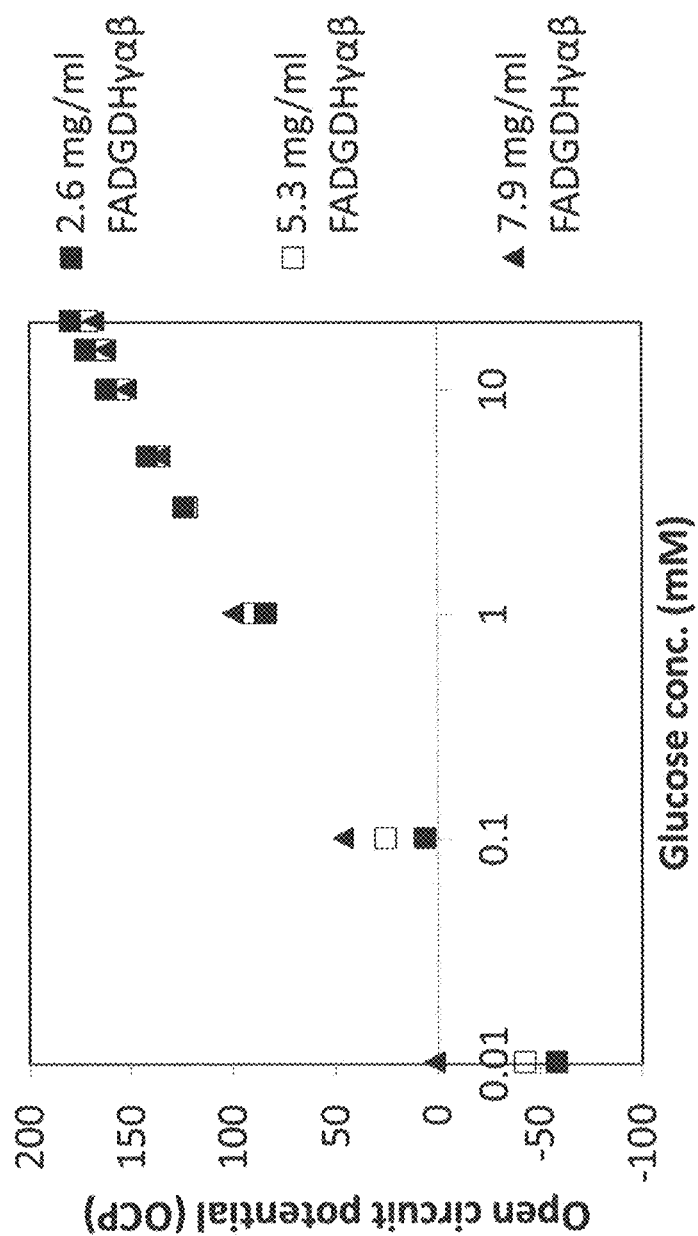
FIG. 5 shows a graph showing evaluation of the glucose concentration dependence in OCP measurement (the measurement was carried out using electrodes having different amounts of GDH immobilized thereon).

The results are shown in FIG. 5.

It was found that the OCP value measured after applying the external potential to the enzyme sensor having the GDH electrode, and performing the enzymatic reaction, is dependent on the glucose concentration.

Example 2

2-1. Preparation of GDH-SAM Sensor
1. Overnight piranha treatment of the surface of an Au electrode (surface area, 7 mm²), and washing with acetone
2. Overnight immersion of the electrode in 10 μM DSH solution for DSH modification

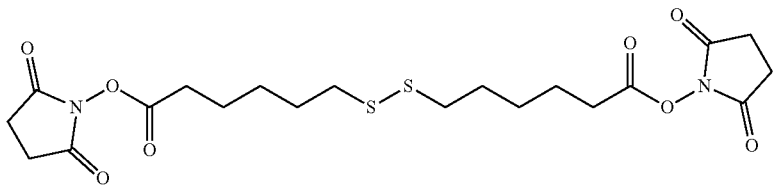

Dithiobis(succinimidyl hexanoate): DSH

3. Overnight immersion in a glucose dehydrogenase solution (26.3 mg/mL FADGDH γαβ/100 mM PPB (pH 7.0)) for immobilization of GDH on the electrode through SAM 2-2. Preparation of GDH-MWCNT Sensor
1. Application of a multi-walled carbon nanotube (MWCNT) dispersion (trade name, Meijo Nano Carbon MWNT INK (MW-I); concentration, 2%; 2 μL) to an Au electrode (surface area, 7 mm²)
2. Application of an aqueous *Burkholderia cepacia* glucose dehydrogenase (FADGDH γαβ) solution (0.013 mg/mL, 7 μL) and drying (for a control, application of a BSA solution)
3. Treatment with 25% glutaraldehyde (GA) vapor for 1 hour to perform cross-linking of GDH to the electrode 2-3. Potential Measurement Each enzyme electrode prepared as described above (GDH-mesoporous carbon in Example 1 (MesoPC), GDH-SAM in Example 2-1, or GDH-MWCNT in Example 2-2) was combined with a counter electrode and a reference electrode (both of which were Ag/AgCl) to provide a biosensor, and a potential of +100 mV (vs Ag/AgCl) was applied to the enzyme electrode (1 time of 10 seconds of application), followed by addition of glucose at various concentrations to cause enzymatic reaction, and measurement of the open circuit potential.

For each electrode, the relationship between the glucose concentration and the OCP value was plotted.

Figure 6:
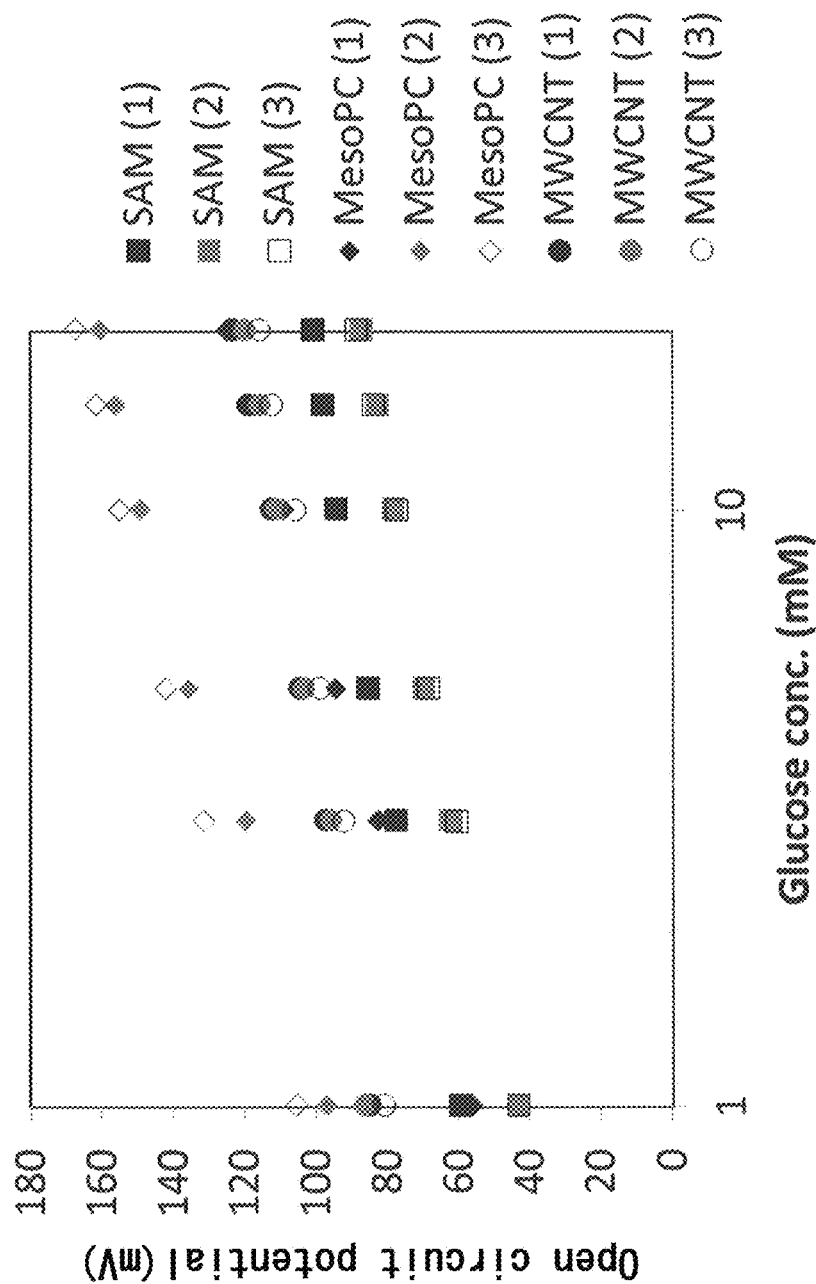
FIG. 6 shows a graph showing results of evaluation of the glucose concentration dependence using enzyme electrodes prepared by various immobilization methods (n=3 for each case).

The results are shown in FIG. 6. For all electrodes, glucose concentration dependence of the OCP was confirmed.

Example 3

Preparation of GDH-GC Sensor

1. Grinding and washing of the surface of a glassy carbon (GC) electrode
2. Overnight immersion in a glucose dehydrogenase solution (26.3 mg/mL FADGDH γαβ/100 mM PPB (pH 7.0)) for immobilization of GDH on the electrode (for a control, use of a non-direct electron transfer type GDH containing no cytochrome)
3. Treatment with 25% glutaraldehyde (GA) vapor for 1 hour to perform cross-linking of GDH to the electrode Surface Potential Measurement The enzyme electrode prepared as described above was combined with a counter electrode and a reference electrode (both of which were Ag/AgCl) to provide a biosensor, and a potential of +100 mV (vs Ag/AgCl) was applied to the enzyme electrode (1 time of 10 seconds of application), followed by addition of glucose at a predetermined concentration to cause enzymatic reaction, and measurement of the open circuit potential. This step was repeatedly carried out.

As a control, a biosensor comprising an enzyme electrode to which a non-direct electron transfer type GDH was immobilized, as well as a counter electrode and a reference electrode, was used. A potential of +100 mV was applied to the electrode (1 time of 10 seconds of application), followed by addition of glucose at a predetermined concentration to cause enzymatic reaction, and measurement of the open circuit potential. This step was repeatedly carried out.

Figure 7:
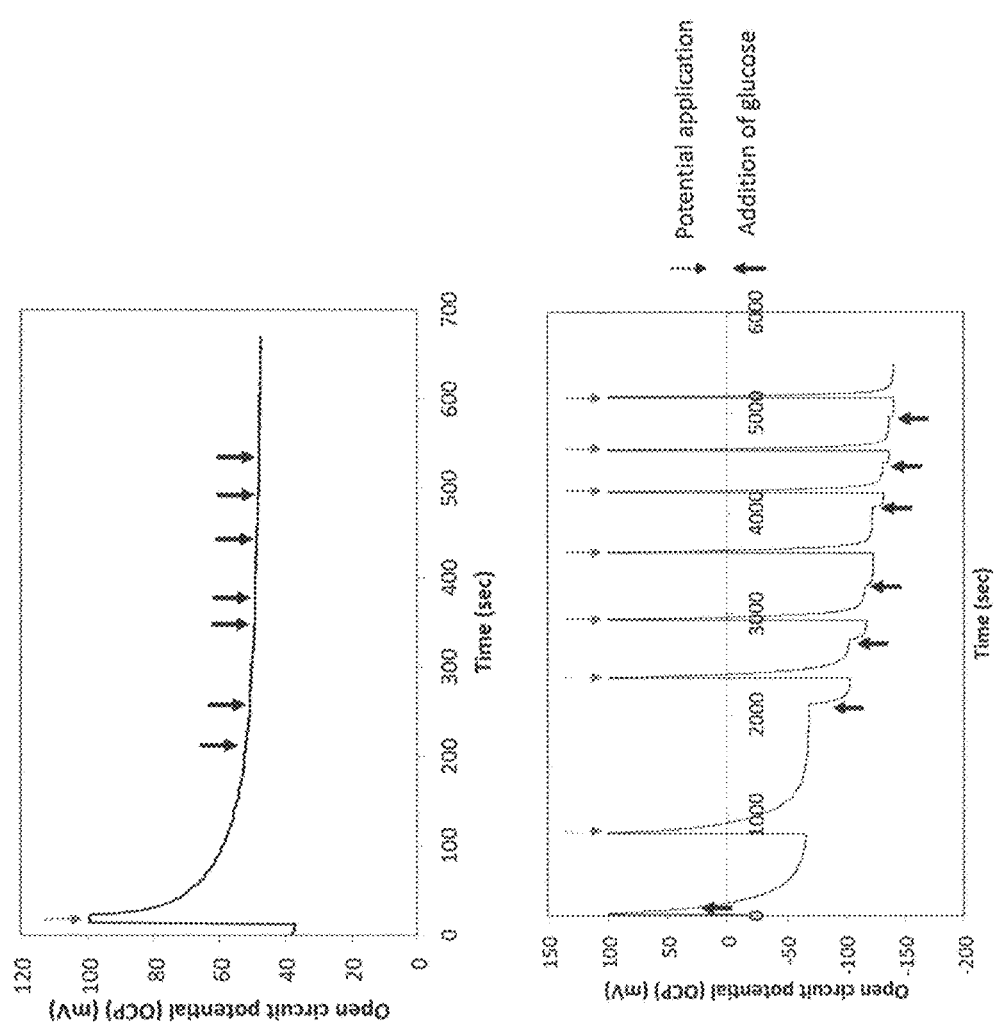
FIG. 7 shows graphs showing results of OCP measurement using GDH immobilized on a glassy carbon electrode surface (upper panel, non-direct electron transfer type; lower panel, direct electron transfer type).

The results are shown in FIG. 7.

As a result, since no OCP change occurred due to the addition of glucose in the case where the FAD-GDH was of a non-direct electron transfer type (FIG. 7, upper panel), the glucose response according to the present invention (FIG. 7, lower panel) was thought to be dependent on the change in the conditions of the electron transfer unit that occurred when the enzyme oxidized glucose to a reduced form.

Example 4

4-1. Measurement of OCP Responding Time

Using the sensor comprising FADGDH γαβ prepared in Example 1, measurement was carried out for various lengths of time of application of a potential (+100 mV vs Ag/AgCl), and the responding time (the time required for the OCP to show a constant value depending the glucose concentration) at each glucose concentration was investigated.

Figure 8:
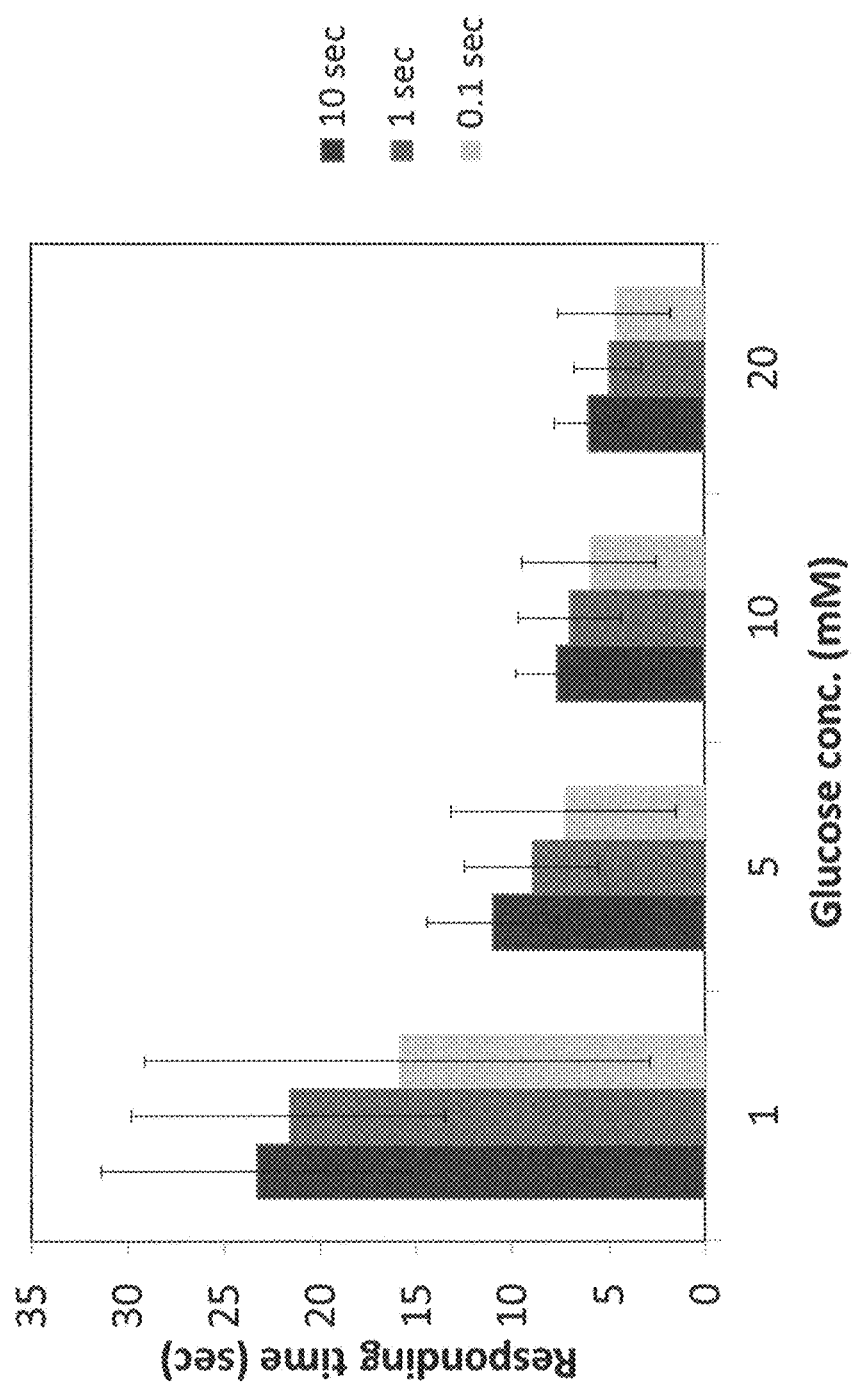
FIG. 8 shows a graph showing results of investigation of the relationship between the period of application of an oxidation potential of +100 mV and the OCP glucose response rate (measurement at glucose concentrations of 1, 5, 10, and 20 mM).

The results are shown in FIG. 8.

It was found that, while the responding time of OCP is long at low concentration of glucose, the responding time decreases as the potential application time decreases, so that the responding time of OCP can be controlled by the potential application time.

4-2. Comparison of Measurement Results Between Cases with or without Application of Potential Using the sensor comprising FADGDH γαβ prepared in Example 1, a potential (+100 mV vs Ag/AgCl) was applied (for 1 second), or no potential was applied. Thereafter, glucose was added thereto at a predetermined concentration to cause enzymatic reaction, and the open circuit potential was measured (3 times for each case).

Figure 9:
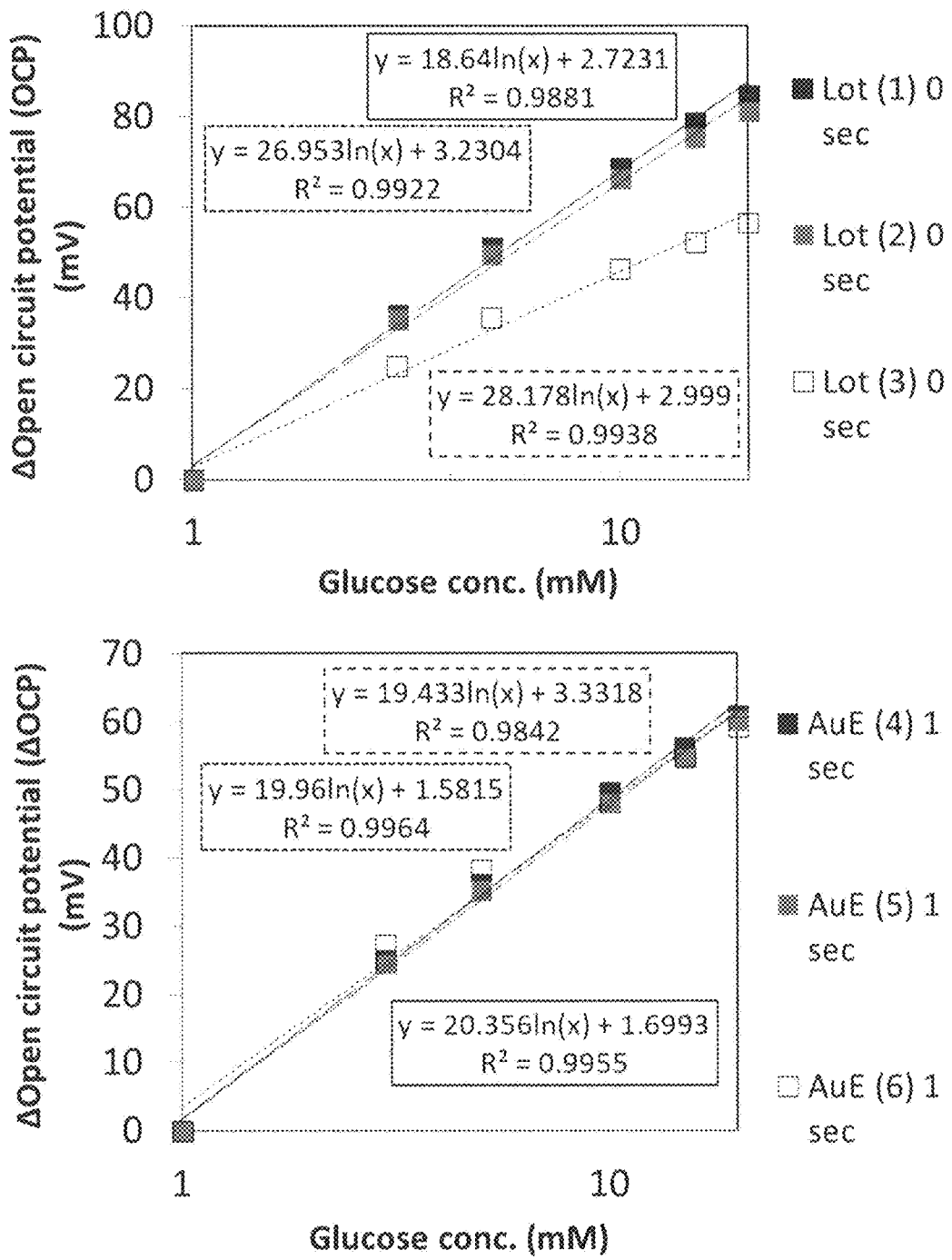
FIG. 9 shows graphs showing results of investigation of the difference in the OCP glucose response between cases with or without application of an oxidation potential of +100 mV (upper panel, no discharge; lower panel, 1 sec of discharge).

The results are shown in FIG. 9.

It was suggested, as a result, that a large variation occurs among measurement results in cases where no potential is applied, but that the inter-sensor difference can be significantly reduced by allowing discharge by application of a potential, thereby enabling more accurate glucose measurement.

As a result of performing the same experiment while changing the potential application time and the glucose concentration, it could be confirmed, as shown by the standard deviation for the results of three times of measurement in Table 1, that variation of the amount of potential change can be suppressed by 0.1 to 10 seconds of application of a potential, compared to cases where no potential is applied.

TABLE 1

|  | 3 mM | 5 mM | 10 mM | 20 mM |
|---|---|---|---|---|
| 0 sec | 5.08 | 6.91 | 10.04 | 12.58 |
| 0.1 sec | 1.24 | 0.91 | 3.33 | 3.43 |
| 1 sec | 1.14 | 1.30 | 0.73 | 0.62 |
| 10 sec | 1.88 | 2.60 | 1.59 | 1.61 |

Example 5

Continuous Glucose Measurement

The sensor comprising FADGDH γαβ prepared in Example 2-1 was immersed in 20 mM glucose solution (100 mM PPB (pH 7.0)), and continuous measurement of the OCP was carried out at 37° C. with stirring at 250 rpm according to the following program.

Figure 10:
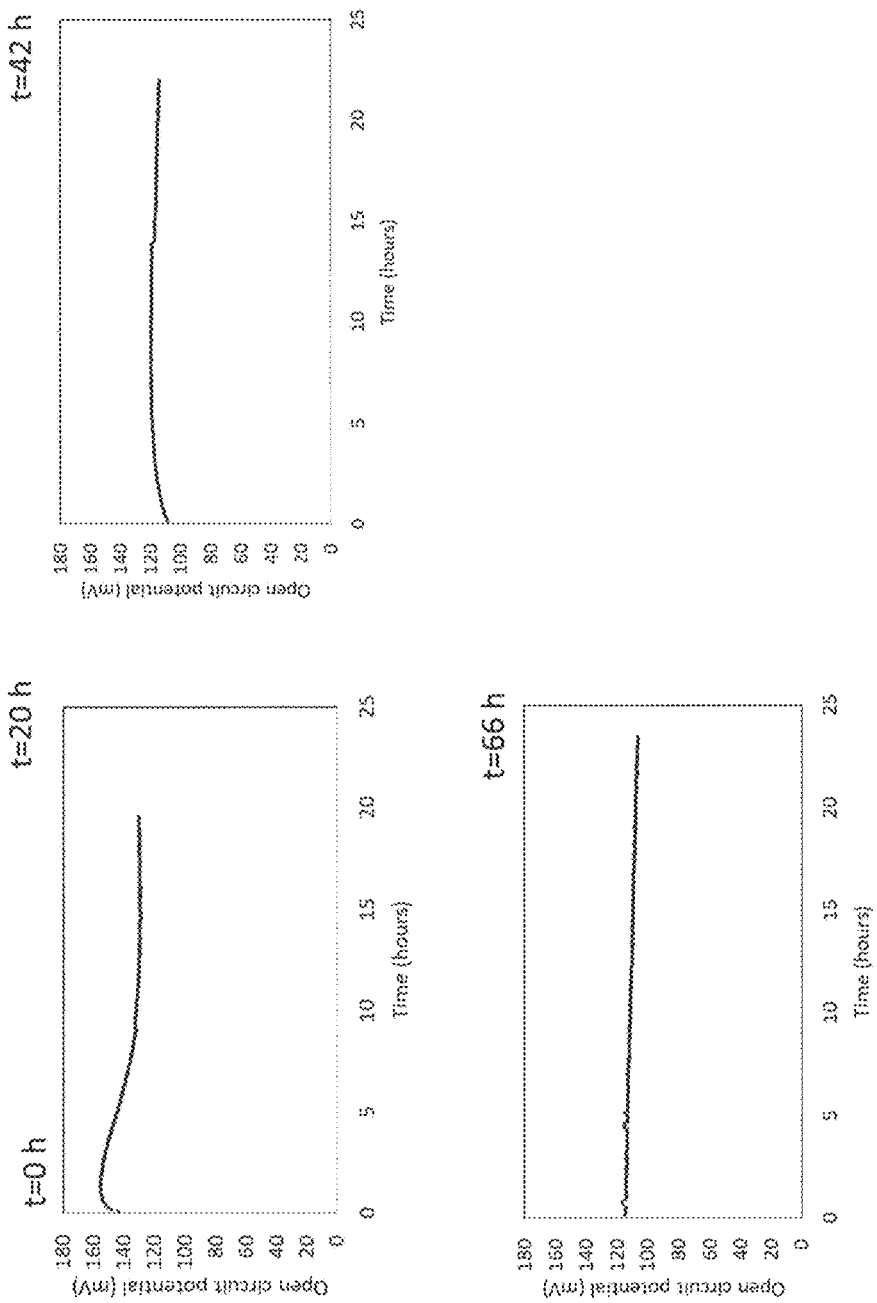
FIG. 10 shows graphs showing results of 5 days of continuous OCP measurement using an enzyme-immobilized electrode with application of an oxidation potential (+100 mV) in a 20 mM glucose solution (the results are separately shown for 0 to 20 h, 20 to 42 h, and 42 to 66 h).

1. +100 mV (vs Ag/AgCl) for 10 sec
2. OCP measurement for 5 min (sampling at 1-second intervals)
3. Repeating of the above process The results are shown in FIG. 10.

The results indicate that a stable constant signal can be obtained by the method of the present invention employing application of a potential for measurement of the OCP, even in long-term measurement in which common amperometric methods show signal attenuation.

Figure 11:
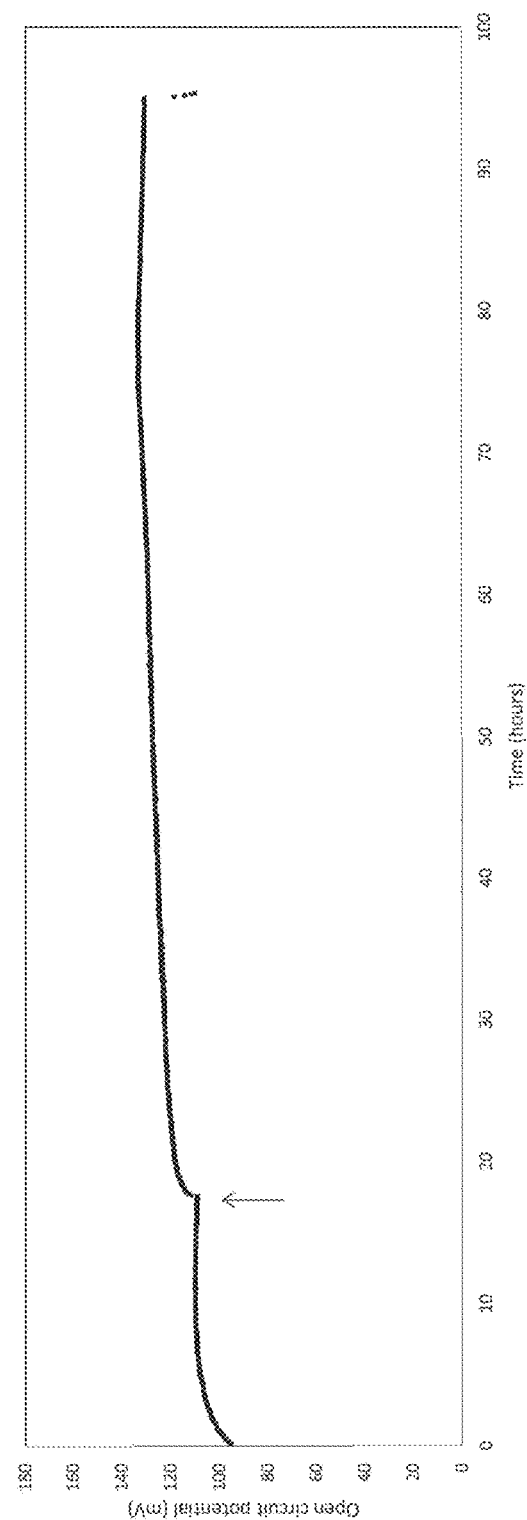
FIG. 11 shows a graph showing measurement results of continuous OCP measurement using an enzyme-immobilized electrode, during which application of an oxidation potential was stopped. The timing when the application of the oxidation potential was stopped is indicated with an arrow.

When the application of the oxidation potential was stopped in the middle of the continuous measurement, the OCP tended to increase even at the constant glucose concentration. It was thus found that accurate measurement requires application of a potential (FIG. 11).

DESCRIPTION OF SYMBOLS

A . . . Biosensor
10 . . . Substrate
11 . . . Counter electrode
11a . . . Lead section
12 . . . Working electrode
12a . . . Lead section
13 . . . Detection section
14 . . . Insulating layer
15 . . . Spacer
16 . . . Cover
17 . . . Sample supply section
18 . . . Air hole
B . . . Measuring apparatus
20 . . . Output section
21 . . . Power supply device
22 . . . Control section
23 . . . Arithmetic section 24 . . . Potentiostat
25 . . . Display section unit
26 . . . Battery
27 . . . Glucose sensor
28 . . . Control computer
29 . . . Potentiometer
30 . . . Substrate
CR, W . . . Terminal While the invention has been described in detail with reference to exemplary embodiments thereof, it will be apparent to one skilled in the art that various changes may be made, and equivalents employed, without departing from the scope of the invention. Each of the aforementioned documents as well as JP2018-097997 is incorporated by reference herein in its entirety.

What is claimed is:

1. A method for quantifying a target substance comprising:
    bringing a sample containing the target substance into contact with a biosensor which comprises: (i) an enzyme electrode on which an oxidoreductase is immobilized, wherein the oxidoreductase is an oxidoreductase capable of direct transfer of electrons with the enzyme electrode, or the oxidoreductase is modified with an electron acceptor in which the electron acceptor is chemically bound to the oxidoreductase, and (ii) a counter electrode;
    measuring an open circuit potential between the enzyme electrode and the counter electrode due to an oxidation reaction of the target substance catalyzed by the oxidoreductase, wherein a potential between the enzyme electrode and the counter electrode is applied before measuring the open circuit potential; and
    calculating the concentration of the target substance based on a value of the measured open circuit potential.

2. The method according to claim 1, wherein the potential applied between the enzyme electrode and the counter electrode is not less than −100 mV as evaluated using a silver/silver chloride electrode as a reference.

3. The method according to claim 1, wherein the potential between the enzyme electrode and the counter electrode is applied for not less than 0.1 seconds.

4. The method according to claim 1, wherein the oxidoreductase is an oxidoreductase containing an electron transfer subunit or an electron transfer domain.

5. The method according to claim 1, wherein the electron transfer subunit or the electron transfer domain contains heme.

6. The method according to claim 1, wherein the potential between the enzyme electrode and the counter electrode is applied after bringing the sample into contact with the biosensor, and is followed by measuring the open circuit potential.

7. The method according to claim 1, wherein a cycle of application of the potential between the enzyme electrode and the counter electrode and measurement of the open circuit potential is repeated.

8. The method according to claim 1, wherein the substance is glucose, and the oxidoreductase is glucose dehydrogenase.

9. The method according to claim 8, wherein the sample is a biological sample.

10. The method according to claim 9, wherein the sample is blood or urine.

11. The method of claim 1, wherein the sample is brought in contact with the biosensor by implanting the biosensor in a body to place the biosensor in a state where the biosensor is in contact with the sample.

12. The method of claim 1, wherein the oxidoreductase is immobilized on the enzyme electrode through a monolayer-forming molecule, a conductive polymer, or a cross-linking agent.

13. The method of claim 12, wherein the oxidoreductase is immobilized on the enzyme electrode through the cross-linking agent.

14. The method of claim 12, wherein the oxidoreductase is immobilized on the enzyme electrode through the monolayer-forming molecule.

15. The method of claim 1, wherein the oxidoreductase is the oxidoreductase capable of direct transfer of electrons with the enzyme electrode.

16. The method of claim 1, wherein the oxidoreductase is the oxidoreductase modified with an electron acceptor in which the electron acceptor is chemically bound to the oxidoreductase.

17. The method of claim 1, wherein the biosensor has a single enzyme electrode.

18. The method of claim 1, wherein the calculating of the concentration of the target substance is based on only the value of the measured open circuit potential.

19. An apparatus for measuring a target substance comprising:
    a biosensor comprising: (i) an enzyme electrode on which an oxidoreductase is immobilized, wherein the oxidoreductase is an oxidoreductase capable of direct transfer of electrons with the enzyme electrode, or the oxidoreductase is modified with an electron acceptor in which the electron acceptor is chemically bound to the oxidoreductase, and (ii) a counter electrode;
    a control section configured to control the application of a potential to the enzyme electrode of the biosensor;
    a measurement section configured to measure the an open circuit potential between the enzyme electrode and the counter electrode of the biosensor;
    an arithmetic section configured to calculate the concentration of the target substance from a value of the measured open circuit potential ; and
    an output section configured to output the concentration of the calculated target substance.

* * * * *